United States Patent [19]

Gupton, III et al.

[11] 4,018,771
[45] Apr. 19, 1977

[54] PROCESS FOR THE PRODUCTION OF 2-ALKYL OR 2-CYCLOALKYL-4-METHYL-6-HYDROXYPYRIMIDINES

[75] Inventors: John T. Gupton, III, Jamestown; Alex M. Jelenevsky, Nashville; Teruko U. Miyazaki, Greensboro; Harris E. Petree, Kernersville, all of N.C.

[73] Assignee: Ciba-Geigy Corporation, Ardsley, N.Y.

[22] Filed: Aug. 23, 1976

[21] Appl. No.: 711,035

[52] U.S. Cl. .................. 260/251 R; 260/557 R; 260/561 R
[51] Int. Cl.² ................................ C07D 239/34
[58] Field of Search ......................... 260/251 R

[56] References Cited
UNITED STATES PATENTS 3,050,523   8/1962   Erner et al. .................. 260/251 R

OTHER PUBLICATIONS

Brown et al., "The Pyrimidines" (1962) p. 228.

Primary Examiner—Elbert L. Roberts
Assistant Examiner—D. R. Phillips
Attorney, Agent, or Firm—Karl F. Jorda

[57] ABSTRACT

Production of 2-alkyl or 2-cycloalkyl-4-methyl-6-hydroxy pyrimidines by first reacting diketene and lower alkanoic or cycloalkanoic acid amides in the presence of catalytic amounts of Lewis bases or Lewis or Brønsted acids, followed by treating the N-acetoacetyl (lower) alkanoic or cycloalkanoic acid amide intermediates with ammonia in the presence of acid catalysts.

10 Claims, No Drawings

PROCESS FOR THE PRODUCTION OF 2-ALKYL OR 2-CYCLOALKYL-4-METHYL-6-HYDROXYPYRIMIDINES

These substituted hydroxypyrimidines have been produced in commercial practice in a laborious multistep manner as follows:

(a) Iminoethene Step:

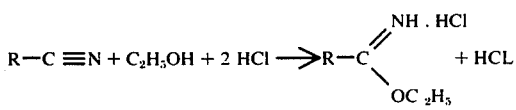

b) Amidine Step:

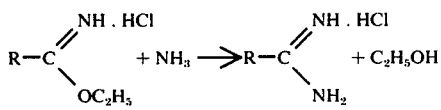

c) Ring-closure Step:

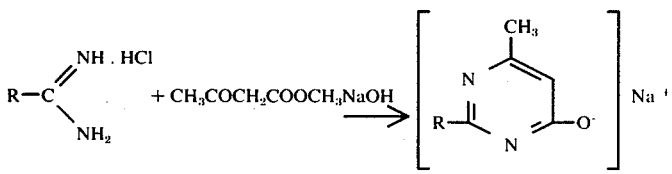

d) Neutralization Step:

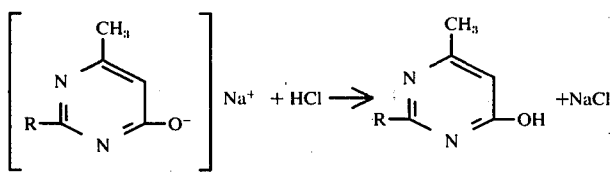

DETAILED DISCLOSURE

The present invention relates to a new and improved manufacturing process for 2-alkyl or 2-cycloalkyl-4-methyl-6-hydroxypyrimidines of the general formula

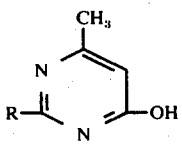

(I)

wherein R represent an alkyl or a cycloalkyl group.

Alkyl groups denoted by R are straight-chain or branched-chain groups having preferably 1 to 4 carbon atoms, such as, methyl, ethyl, n-propyl, isopropyl, n-butyl, secondary butyl, isobutyl or tertiary butyl.

Cycloalkyl groups denoted by R have 3 to 6 ring carbon atoms. Preferred cycloalkyl groups are cyclopropyl, cyclopentyl or cyclohexyl.

The compounds of formula I have particular importance as intermediates for the preparation of, e.g., phosphoric acid esters of substituted hydroxypyrimidines as disclosed and claimed in U.S. Pat. No. 2,754,243 and, in particular, O,O-diethyl-O-(2-isopropyl-4-methyl-6-pyrimidyl)-thiophosphate (Diazinon), which has great commercial value by virtue of its well-established insecticidal and acaricidal activity and consequent usefulness in pest control.

In the above formulae R has the same meaning as given for Formula I.

More recently, this conventional manufacturing process has been improved and optimized by way of a continous ring-closure/neutralization process as disclosed and claimed in (Ser. No. 598,100) and alternate processes for the preparation of the subject hydroxypyrimidines have been published in the Japanese patent literature.

For instance, according to Japanese Pat. No. 557,103, the subject hydroxypyrimidines can be prepared by various heat treatments from β-acylaminocrotonamides which are made from β-aminocrotonamide (derived from diketene and ammonia) and acid anhydrides or acid halides and according to published Japanese Patent Application Sho 48-39,942, they can be produced by reacting β-aminocrotonamide and an organic acid ester in the presence of certain alkaline reactants, such as, alkali metals or alkali metal alcoholates.

However, all of these prior art procedures leave something to be desired from the standpoint of efficient and economical large-scale commercial manufacturing.

In the search for better and cheaper process technology for the manufacture of the subject hydroxypyrimidines and the phosphoric acid ester derivatives made therefrom, it has now been found, surprisingly and unexpectedly — and this forms the principal object of this invention — that these hydroxypyrimidines can be synthesized in a completely novel way which involves fewer steps, milder conditions, simpler equipment and less expensive reactants. It has been found that this can be accomplished by reacting diketene and lower alkanoic or cycloalkanoic acid amides in a solvent and in the presence of an acid or base catalyst to form N-acetoacetyl substituted (lower)alkanoic or cycloalkanoic acid amides which are then converted by ammonia to the subject hydroxypyrimidines again in a solvent and in the presence of a catalyst in accordance with the following reaction scheme:

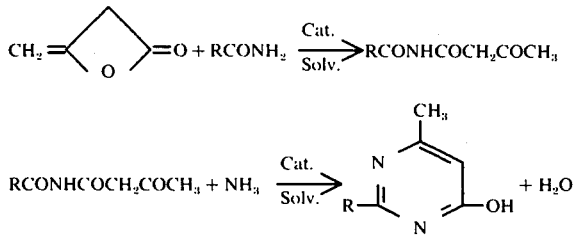

Again, R in the above formulae has the same meaning as given for formula I above.

More specifically, in this novel and improved process diketene and the lower alkanoic or cycloalkanoic acid amide (hereinafter "acid amide") are first reacted to yield a N-acetoacetyl (lower) alkanoic or cycloalkanoic acid amide. This reaction is carried out in an inert organic solvent and in the presence of catalytic amounts of Lewis bases and Lewis and Bronsted acids at elevated temperatures.

With respect to the specific reaction procedure and especially the order of addition of the reactants, it is advantageous to add diketene slowly to an appropriate reaction vessel containing a solution or suspension, heated to an elevated temperature, of the acid amide and the catalyst. Alternatively, diketene, acid amide, solvent and catalyst are simply mixed together also in a conventional reaction vessel at room temperature before heating to an elevated temperature. Additionally, the catalysts can be added to the reaction mixture in incremental amounts.

The starting materials for this inventive process, diketene and acid amide, which are commercially available for accessible, are generally employed in equimolar amounts. However, excess amounts of either reactant, up to about 200 mole % excess, especially of the acid amide, can be employed for the purpose of yield improvement.

The reaction time for this diketene/acid amide reaction is typically from about a quarter of an hour to about eight hours, and preferably about 1 to 2 hours.

The inert organic solvent useful in this diketene/acid amide step can be selected from classes which include, but are not limited to, the following: aromatic hydrocarbons, such as, benzene, toluene, xylene, chlorobenzene, nitrobenzene; chlorinated hydrocarbons, such as, chloroform, carbon tetrachloride, ethylene dichloride, trichloroethylene; tetrachloroethylene; lower alkanoic acids and esters thereof, such as, acetic acid, propionic acid, isobutyric acid, ethyl acetate, ethyl propionate, isobutyl isobutyrate; ethers, such as, tetrahydrofuran, p-dioxane, 1,2-dimethoxyethane; ketones, such as, methyl ethyl ketone, methyl isobutyl ketone, cyclohexanone; and nitriles, such as, acetonitrile, isobutyronitrile, or mixtures thereof. Preferred solvents are aromatic and chlorinated hydrocarbons, especially toluene and trichloroethylene.

other classes or species of solvents, which are liquid at room temperature and have a boiling point of at least 40° C, can also be employed as will be obvious to men skilled in the art.

The catalysts useful in this step are Lewis bases and salts thereof and Lewis and Brønsted acids. Lewis bases and salts thereof can be exemplified by, but are not limited to, the following: tertiary amines and salts thereof: pyridine, pyridine hydrochloride, pyridine acetate, pyridine p-toluenesulfonic acid, dimethylaminopyridine, dimethylaminopyridine hydrochloride, N-methylmorpholine, N-methylpyrrolidine, N-methylpiperidine, α-picoline, triethylamine, triethylamine hydrochloride, tetramethylammonium chloride, poly (4-vinylpyricine/divinylbenzene), poly (4-vinylpyridine/divinylbenzene) hydrochloride, poly(4-vinylpyridine/divinylbenzene) acetate, 1,4-diazobicyclo [2,2,2]octane, 1-azobicyclo[2,2,2]octane; the following tertiary phosphines: triphenyl phosphine, trimethyl phosphite; and also dimethylformamide. Lewis acids can be illustrated by, but are not limited to, the following acids: boron trifluoride etherate, zinc chloride, aluminum chloride. As Brønsted acids can be enumerated, without limiting them thereto, the following oganic and mineral acids: acetic acid, trifluoroacetic acid, isobutyric acid, p-toluenesulfonic acid, hydrogen chloride, sulfuric acid, phosphoric acid. Mixtures of the foregoing acids, e.g., pyridine and pyridine hydrochloride, pyridinium acetate and acetic acid, pyridine and pyridinium p-toluenesulfonate, can also be employed.

Particularly preferred are acetic acid, pyridine, pyridine hydrochloride, and a mixture of the latter two. When pyridine hydrochloride is used as catalyst it is advantageously generated in situ by bubbling dry hydrogen chloride into the solvent, e.g., toluene, containing pyridine. Excess hydrogen chloride is driven off by refluxing this solvent while purging with air.

Typically, about 5 to 50 mol % of the catalyst per mole of diketene and acid amide is employed and preferably about 10 to 30 mole %.

The reaction temperature in this step can vary within the range of about 40° C to 150° C and preferably between about 50° C and 90° C. It depends often on the solvent chosen.

The reaction product of the diketene/acid amide reaction is, as stated above, an N-acetoacetyl (lower) alkanoic or cycloalkanoic acid amide. This product serves as an intermediate in the second or amination/cyclization step with or without isolation.

The second step which involves treating the N-acetoacetyl (lower) alkanoic or cycloalkanoic acid amide intermediate with ammonia also in a solvent and in the presence of a catalyst and at elevated temperatures, accomplishes amination and cyclization of the intermediate to 2-alkyl or 2-cycloalkyl-4-methyl-6-hydroxypyrimidine (via a 3-aminocrotonyl (lower) alkanoic or cycloalkanoic acid amide).

More specifically, this second step where the N-acetoacetyl acid amide intermediate is recovered in a conventional manner from the first step, is carried out by dissolving this intermediate in a heated or refluxing solvent containing the catalyst, followed by sparging in ammonia and accompanied by removal of water for example, by azeotropic distillation. The conversion of the N-acetoacetyl acid amide intermediate to the desired hydroxypyrimidine is almost quantitative.

While amination proceeds rapidly and is completed in a matter of minutes, e.g. 5 to 30 minutes as determined by thin layer chromatography, cyclization takes longer and may be completed only after one to six hours.

As solvents or solvent system there can be used not only the same solvents or same solvent system than can be employed in the first step as enumerated or mentioned above but also such additional classes as aliphatic alcohols, e.g. isobutanol, tertiary butanol, etc. Particularly preferred is toluene.

With respect to the catalysts, it is advantageous to employ acidic substances, i.e. Brønsted acids, such as, acetic acid, trifluoroacetic acid, isobutyric acid, p-toluenesulfonic acid, phosphoric acid and most preferably, acetic acid and p-toluenesulfonic acid.

The acidic catalysts are used in catalytic amounts which typically range between about 25 to 100 mole % per mole of N-acetoacetyl acid amide and preferably between about 30 to 50 mole %.

The reaction temperature in this second step can vary within the range of about 80° to 150° C and preferably between about 95° to 115° C.

It is also entirely feasible to practice the present inventive process in one reactor without isolation and recovery of the N-acetoacetyl acid amide intermediate. Furthermore, it is feasible to practice this process in a semi-continuous as well as continuous fashion.

Isolation and recovery of the desired final product, the 2-alkyl or 2-cycloalkyl-4-methyl-6-hydroxypyrimidine, is carried out and effected in accordance with standard chemical procedures.

It should be understood that various changes and modifications in the procedures described above generally and exemplified below specifically can be made, such changes and modifications being within the scope of the appended claims. It should further be understood that the following examples illustrating specific embodiments are not intended to limit the disclosure.

In these examples, unless otherwise indicated, parts are given by weight and temperatures are in degrees centigrade and "oxypyrimidine" stands for 2-isopropyl-4-methyl-6-hydroxypyrimidine.

EXAMPLE 1

Isobutyramide (8.7 g, 0.1 mole), pyridine (0.8 g, 0.01 mole) and trichloroethylene (100 ml) were mixed in a 250 ml, 3-neck flask equipped with a condenser, a drying tube, a thermometer, a magnetic stirrer and a heating mantle and heated to reflux. Diketene (8.4 g, 0.1 mole) was added dropwise over a 5 minute period. The mixture was refluxed for 2 hours. The contents of the reactor were poured into a 500 ml round-bottom flask and evaporation of the solvent gave 19.4 g of yellow oil which solidified on cooling. The solid was analyzed and the yield of N-acetoacetylisobutyramide was found to be 80.9%. Crude N-acetoacetylisobutyramide (16.5 g) was redissolved in toluene (100 ml) containing acetic acid (3g, 0.05 mole) and placed in a 250 ml, 3-necked flask equipped with a Dean-Stark distilling trap, a condenser connected to a gas bubbler, a thermometer, a gas inlet tube, a magnetic stirrer and a heating mantle. Ammonia gas was bubbled in as the solution was slowly heated to reflux and ammonia was sparged under reflux for 2 hours. The water produced was collected in the Dean-Stark trap by azeotropic distillation. The supernatant liquid was poured into a 500 ml round-bottom flask and the residual solid was extracted with chloroform (100 ml) and the chloroform extract was combined with the supernatant liquid. Evaporation of the solvents produced 12.7 g (82.1%, by weight, of oxypyrimidine) of yellow crystals which amounted to an 80.5% yield.

EXAMPLE 2

Isobutyramide (8.7 g, 0.1 mole), pyridine (0.79 g, 0.01 mole), diketene (8.4 g, 0.1 mole) and toluene (100 ml), were placed in a 250 ml, 3-neck flask equipped with a Dean-Stark distilling trap, a condenser connected to a gas bubbler, a thermometer, a magnetic stirrer and a heating mantle. The mixture was slowly heated to 80° and the temperature range 75°–80° was maintained for 1 hour. After acetic acid (3 g, 0.05 mole) was added, ammonia gas was bubbled in for 1 hour under reflux. The reaction mixture was further refluxed for another hour without ammonia sparging. The insoluble solid was filtered and washed with chloroform (100 ml). Evaporation of the filtrate gave 15.2 g (76.7%, by weight, of oxypyrimidine) of yellow solid having m.p. 140°–158° which amounted to an 76.8% yield.

EXAMPLE 3

Isobutyramide (8.7 g, 0.1 mole), N-methylmorpholine (2.53 g, 0.025 mole) and toluene (100 ml) were placed in a 250 ml, round-bottom flask equipped with a condenser, a drying tube, a thermometer, a magnetic stirrer, a heating mantle and were heated to 95°. Diketene (8.4 g, 0.1 mole) in toluene (25 ml) was added to the solution dropwise over a period of 20 minutes and the reaction mixture was stirred at 95° for 1 hour. The reaction mixture was analyzed and the yield of N-acetoacetylisobutyramide was found to be 40.9%.

EXAMPLE 4

Example 4 was run in a manner analogous to Example 3 with the exception that triphenyl phosphine (6.56 g, 0.025 mole) was used as the catalyst. After heating the reaction mixture for 150 minutes at 95°, analysis of the reaction mixture indicated that N-acetoacetylisobutyramide had formed in 61.9% yield.

EXAMPLE 5

Pyridine (1.58 g, 0.02 mole) and dry toluene (100 ml) were placed in a 250 ml 3-neck flask equipped with a condenser, a drying tube, a Dean-Stark distilling trap, a thermometer, a gas inlet tube, a mechanical stirrer and a heating mantle. The solution was saturated with hydrogen chloride. Air was bubbled in during the reflux to facilitate the removal of hydrogen chloride. After isobutyramide (8.7 g, 0.1 mole) was added, the temperature of the reaction mixture was adjusted to 95° and diketene (8.5 g, 0.1 mole) was added rapidly. An exothermic reaction was observed and the reaction mixture started refluxing. When the exotherm subsided after approximately 10 minutes, the reaction mixture was kept at 93°–95° for 1 hour. Acetic acid (2.0 g, 0.03 mole) was added and ammonia gas was bubbled in at 108° C for 2 hours. Evaporation of the solvent yielded 17.02 g (69.2%, by weight, of oxypyrimidine) of yellow solid which amounted to a 77.5% yield.

EXAMPLE 6

Isobutyramide (8.7 g, 0.1 mole), pyridine hydrochloride (2.31 g, 0.02 mole) and ethyl acetate (100 ml) were placed in a 250 ml, 3-neck flask equipped with a condenser, a drying tube, a magnetic stirrer and a heating mantle and heated to reflux. Diketene (8.4 g, 0.1 mole) was added dropwise over a 5-minute period and the reaction mixture was refluxed for 5 hours. The contents were poured into a 500 ml. r.b. flask and the solvent was evaporated to yield 19.15 g of a light brown oil. The analysis indicated that the yield of N-acetoacetylisobutyramide was 77.7%. The crude N-acetylisobutyramide (16.6 g) in toluene (100 ml) containing acetic acid (4.5 g, 0.075 mole) was placed in a 250 ml, 3-neck flask equipped similarly as in Example 1 and refluxed while sparging ammonia gas for 1.5 hours. After the ammonia was turned off, the reaction mixture was further refluxed for 40 minutes. The work up yielded 13.4 g (73.2%, by weight, of oxypyrimidine) of light yellow solid which amounted to a 75.3% yield.

EXAMPLE 7

Isobutyramide (8.7 g, 0.1 mole), pyridine (0.40 g, 0.005 mole), pyridine hydrochloride (1.73 g, 0.015 mole), diketene (8.4 g, 0.1 mole) and trichloroethylene (100 ml) were placed in a 250 ml, 3-neck flask equipped with a magnetic stirrer, a thermometer, a condenser, a drying tube and a heating mantle. The mixture was slowly heated to 80°, and the temperature range of 75°–81° was maintained for 1 hour. The slightly cooled reaction mixture was poured into a 500 ml, r.b. flask and the solvent was stripped off to give an orange oil. Crude N-acetoacetylisobutyramide thus obtained was dissolved in toluene (100 ml) and placed in a 250 ml, 3-neck flask equipped similarly as in Example 1. After addition of acetic acid (3 g, 0.05 mole), ammonia gas was bubbled in as the reaction mixture was heated at reflux for 1 hour and was further refluxed for 1 hour after the ammonia was turned off. Chloroform (~50 ml) was added to the cooled reaction mixture and the insoluble solid was filtered and washed with chloroform (~ 50 ml). The solvent of the filtrate was stripped off and 15.51 g (81.9%, by weight, of oxypyrimidine) of yellow crystals having m.p. 148°–160° were obtained. The yield was 83.6%.

EXAMPLE 8

4-Dimethylaminopyridine (1.22 g, 0.01 mole) and toluene (50 ml) were placed in a 100 ml, 3-neck flask equipped with a condenser, a drying tube, a gas inlet tube, a magnetic stirrer and a heating mantle. Dry hydrogen chloride was bubbled in for 1 minute and the white 4-dimethylaminopyridine hydrochloride was obtained. The toluene was refluxed and air was bubbled into the solution until no more hydrogen chloride was evolved. The reaction mixture was then cooled to room temperature. Diketene (4.2 g, 0.05 mole) and isobutyramide (4.2 g, 0.05 mole) were added and the reaction mixture was heated and the temperature range of 90°–99° was maintained for 1 hour. Acetic acid (1.5 g, 0.025 mole) was added and N-acetoacetylisobutyramide was ammoniated and cyclized to oxypyrimidine in the same manner as in Example 1. 8.19 g of a yellow solid (64.5%, by weight, of oxypyrimidine) having m.p. 132°–153° was obtained. The yield was 69.5%.

EXAMPLE 9

A 250 ml, three-necked, round-bottom flask was equipped with a condenser, drying tube, magnetic stirrer and heating mantle. Into the flask was placed toluene (100 ml), isobutyramide (8.7 g, 0.10 mole) and triethylamine hydrochloride (3.44 g, 0.035 mole). The mixture was heated to 95° and diketene (8.40 g, 0.10 mole) was added over a 5 minute period. After heating at 95° for 4 hours, analysis of the reaction mixture indicated N-acetoacetylisobutyramide had formed in 56.5% yield.

EXAMPLE 10

Isobutyramide (8.7 g, 0.1 mole), pyridine (0.4 g, 0.005 mole), pyridine hydrochloride (1.73 g, 0.015 mole) and toluene (100 ml) were placed in a 250 ml, 3-neck flask equipped similarly as in Example 2. The mixture was heated to 70° and maintained at this temperature. Diketene (8.4 g, 0.1 mole) was added dropwise over a period of 10 minutes. At the end of the diketene addition, a clear yellow solution was obtained, and it was stirred at 69°–71° for 2 hours. Acetic acid (3 g, 0.05 mole) was added to the reaction mixture, a gas inlet tube was installed and ammonia gas was bubbled in as the temperature of the reaction mixture was allowed to rise to reflux. After 1 hour, ammonia sparging was stopped and the reaction mixture was further refluxed for 1.8 hours. Oxypyridimine crystallized out and was dissolved by adding chloroform (~ 50 ml). The insoluble solid was removed by filtration and washed with chloroform ~ 50 ml). Evaporation of the filtrate yielded 15 g (86%, by weight, of oxypyrimidine) of yellow crystals m.p. 157°–164° which amounted to an 85.4% yield.

EXAMPLE 11

Isobutyramide (8.7 g, 0.1 mole) was dissolved in acetic acid (15 ml) in a 250 ml, 3-neck, r.b. flask equipped with a condenser, a drying tube, a mechanical stirrer and a heating mantle. Diketene (9.2 g, 0.11 mole) was added dropwise over a period of 20 minutes. The reaction mixture was refluxed for 0.5 hour and cooled to room temperature. After addition of toluene (100 ml), a Dean-Stark distilling trap and a gas inlet tube were installed. Ammonia gas was bubbled in as the reaction mixture was slowly heated to reflux. Ammonia was turned off after 1 hour and the reaction mixture was further refluxed for another hour. The contents of the reactor were transferred to a 500 ml, r.b. flask and the solvent was stripped off on the rotary evaporator. The crude product (20.3 g) contained 49.4% by weight oxypyrimidine which amounted to a 66% yield (based on isobutyramide).

EXAMPLE 12

Isobutyramide (8.7 g, 0.1 mole) and isobutyric acid (30 ml) were placed in a 100 ml, 3-neck flask equipped similarly as in Example 1 and heated to 100°. Diketene (8.4 g, 0.1 mole) was added dropwise over a period of 5 minutes and the reaction mixture was kept at 100°–110° for 1.5 hour. The reaction mixture was analyzed and the yield of N-acetoacetylisobutyramide was found to be 63.1%.

EXAMPLE 13

A 250 ml, three-necked, round bottom flask, was equipped with a condenser, drying tube, mechanical stirrer, gas inlet tube, thermometer and heating mantle. Toluene (100 ml) was introduced and hydrogen chloride gas was bubbled through the solvent until the solution was saturated. Isobutyramide (8.70 g, 0.10 mole) was added and the mixture was heated to 92°. Diketene (8.40 g, 0.10 mole) was added over a 6 minute period and after heating for 15 minutes, a 38.7% yield of N-acetoacetylisobutyramide was obtained.

EXAMPLE 14

A 250 ml, three-necked, round-bottom flask was equipped with a condenser, drying tube, magnetic stirrer and a heating mantle. Into the flask was placed toluene (100 ml), isobutyramide (8.70 g, 0.10 mole), boron trifluoride etherate (1.42 g, 0.01 mole), and acetic acid (20 ml). Diketene (8.40 g, 0.10 mole) was added and the mixture was stirred at room temperature for 1 hour. The mixture was then heated for 2 hours at reflux and analysis of the crude reaction mixture indicated that N-acetoacetylisobutyramide had formed in 30.3% yield.

EXAMPLE 15

Example 15 was run in a manner analogous to Example 14 with the exception that acetic acid (100 ml) was used as the solvent, zinc chloride (1.36 g, 0.01 mole) was used as the catalyst, and a nitrogen atmosphere was employed. After the addition of diketene (8.40 g, 0.10 mole) and heating the mixture at reflux for 1 hour, a 14.7% yield of N-acetoacetylisobutyramide was obtained.

EXAMPLE 16

10.26 g of 83.8% pure N-acetoacetylisobutyramide (0.05 mole), acetic acid (3 g, 0.05 mole) and toluene (100 ml) were placed in a 250 ml, 3-neck flask equipped with a Dean-Stark distilling trap, a condenser connected to a gas bubbler and a gas inlet tube, a magnetic stirrer and a heating mantle. The solution was heated to reflux while sparging ammonia gas. While the reaction mixture was refluxed for 1.5 hours, the water produced was collected in the Dean-Stark trap by azeotropic distillation. Ammonia sparging was stopped and the reaction mixture was further refluxed for 0.5 hours and cooled. The solid was filtered and wased with warm benzene (120 ml). Evaporation of the filtrate produced 8.69 g (85.4%, by weight, of oxypyrimidine) of slightly green needles having m.p. 156°–164° which amounted to a 97.5% yield.

EXAMPLE 17

Pyridine (7.9 g, 0.1 moles) was placed in 300 ml of dry toluene containing 43.5 g (0.5 moles) of isobutyramide. The solution was saturated with hydrogen chloride gas and then heated to reflux to remove any excess hydrogen chloride. Air was bubbled in during the reflux to facilitate the removal of hydrogen chloride. The temperature of the reaction mixture was adjusted to 95° and 42.4 g (0.5 moles) of diketene was rapidly added. The reaction temperature rose to the refluxing temperature of toluene and maintained itself for 12 minutes. The reaction mixture was heated an additional 30 minutes and an equivalent of acetic acid (0.1 moles) was added. Ammonia gas was bubbled into the reaction mixture at such a rate as to maintain an azeotropic removal of water. After 2 hours the reaction was cooled to r.t. and the solvent was removed in vacuo to yield a solid which was triturated with cold water, filtered and dried. The yield of oxypyrimidine for this process was 76.2%.

EXAMPLE 18

An acetic acid/toluene mixture (1:1 by volume) was employed as the solvent. Isobutyramide (8.7 g, θ 0.1 mole), diketene (8.4 g, θ 0.1 mole) and solvent (100 ml) were mixed and refluxed for 2 hours. The product thus obtained was converted to oxypyrimidine "in situ". Toluene (100 ml) was added and ammonia was sparged in under reflux for 1.5 hours, followed by refluxing for 0.5 hours with removal of water by azeotropic distillation. This procedure gave a 57.4% overall yield of isolated oxypyrimidine based on diketene. Isobutanol, tertiary butanol and diglyme (bis-2-methoxyethyl ether) were also employed similarly as the solvent in the second step.

EXAMPLE 19

Toluene (500 ml) containing pyridine (0.125 moles) was mixed with isobutyramide (0.5 moles) and heated to 108°. Diketene (0.5 moles, diluted with 125 ml of the solvent) was added dropwise over a period of 60 minutes. After the addition of diketene was completed, the reaction mixture was heated for 30 minutes. The product was converted to oxypyrimidine by addition of acetic acid (0.25 moles) followed by amination with ammonia and cyclization. The overall yield of oxypyrimidine obtained was 67%. Besides toluene, also p-dioxane was employed as solvent in this procedure.

If in the above process wherein the isopropyl embodiment has been illustrated, cyclopropane carboxylic acid amide is employed in lieu of isobutyramide, 2-cyclopropyl-4-methyl-4-hydoxypyrimidine is obtained in an analogous manner via the N-acetoacetyl cyclopropane carboxylic acid amide intermediate.

What is claimed is:

1. A process for the preparation of a 2-alkyl or 2-cycloalkyl-4-methyl-6-hydroxypyrimidine of the formula

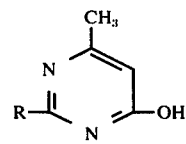

wherein R represents alkyl of 1 to 4 carbon atoms and cycloalkyl of 3 to 6 carbon atoms, which comprises 1. reacting diketene and an acid amide of the formula

wherein R has the same meaning as given above, in an inert organic solvent at a temperature ranging from about 40° C to 150° C and in the presence of a catalytic amount of a Lewis base or salt thereof or Lewis or Bronsted acid, to form a N-acetoacetyl acid amide of the formula

wherein R has the same meaning as given above and 2. reacting said N-acetoacetyl acid amide with ammonia in an inert organic solvent at a temperature ranging from about 80° to 150° C and in the presence of a Brønsted acid.

2. A process according to claim 1, wherein R is isopropyl.

3. A process according to claim 1, wherein the solvent is toluene or trichloroethylene.

4. A process according to claim 1, wherein the catalyst in step 1) is acetic acid, pyridine, pyridine hydrochloride or mixtures thereof.

5. A process according to claim 4, wherein the catalyst is pyridine.

6. A process according to claim 4, wherein the catalyst is a mixture of pyridine and pyridine hydrochloride.

7. A process according to claim 1 wherein the catalyst in step 2) is acetic acid or p-toluenesulfonic acid.

8. A process according to claim 1 wherein the reaction temperature is between 50° and 90° C in step 1) and about 90° and 115° C in step 2).

9. A process according to claim 1 which is carried out in one reactor without isolation of the N-acetoacetyl intermediate.

10. A process according to claim 1 wherein R is isopropyl, the solvent is toluene or trichloroethylene in step 1 and toluene in step 2, the catalyst is pyridine, pyridine hydrochloride or a mixture thereof in step 1 and acetic acid in step 2 and the temperature is between 50° and 90° C in step 1 and about 95° and 115° C in step 2.

* * * * *

UNITED STATES PATENT AND TRADEMARK OFFICE
CERTIFICATE OF CORRECTION

PATENT NO. : 4,018,771
DATED : April 19, 1977
INVENTOR(S) : John T. Gupton, III, et al It is certified that error appears in the above-identified patent and that said Letters Patent are hereby corrected as shown below:

Column 2, "(a) Iminoethene Step:" should read
-- a) Iminoether Step: --
and that portion of the formula
"
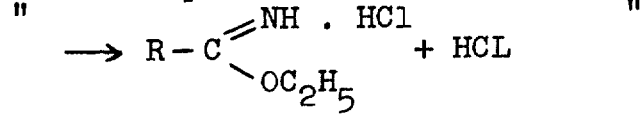
+ HCL
"

should read
--
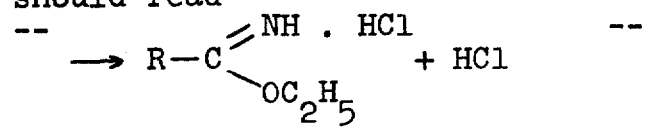
+ HCl
--

Column 4, line 13, "(4-vinylpyricine/divinylbenzene)" should read -- (4-vinylpyridine/divinylbenzene) --.

Column 4, line 23, "oganic" should read -- organic --.

Column 9, line 37, "wased" should read -- washed --.

Signed and Sealed this

Twentieth Day of September 1977

[SEAL]

Attest:

RUTH C. MASON
Attesting Officer

LUTRELLE F. PARKER
Acting Commissioner of Patents and Trademarks